US006880558B2

(12) United States Patent
Perez

(10) Patent No.: US 6,880,558 B2
(45) Date of Patent: Apr. 19, 2005

(54) METHOD OF LIFTING AN EPITHELIAL LAYER AND PLACING A CORRECTIVE LENS BENEATH IT

(75) Inventor: Edward Perez, Menlo Park, CA (US)

(73) Assignee: Tissue Engineering Refractions, Inc., Menlo Park, CA (US)

( * ) Notice: Subject to any disclaimer, the term of this patent is extended or adjusted under 35 U.S.C. 154(b) by 125 days.

(21) Appl. No.: 10/243,121

(22) Filed: Sep. 13, 2002

(65) Prior Publication Data

US 2003/0083743 A1 May 1, 2003

Related U.S. Application Data

(63) Continuation of application No. PCT/US01/22633, filed on Jul. 18, 2001, and a continuation-in-part of application No. 09/618,580, filed on Jul. 18, 2000, now Pat. No. 6,544,286.

(51) Int. Cl.⁷ .............................................. A61B 19/00
(52) U.S. Cl. ....................... 128/898; 623/5.11; 606/107
(58) Field of Search ................................ 623/4.1, 5.11; 128/898

(56) References Cited

U.S. PATENT DOCUMENTS

| 4,346,482 A | 8/1982 | Tennant et al. |
|---|---|---|
| 4,646,720 A | 3/1987 | Peyman et al. |
| 4,662,881 A | 5/1987 | Nordan |
| 4,676,790 A | 6/1987 | Kern |
| 4,715,858 A | 12/1987 | Lindstrom |
| 4,793,344 A | 12/1988 | Cumming et al. |
| 5,171,318 A | 12/1992 | Gibson et al. |
| 5,192,316 A | 3/1993 | Ting |
| 5,213,720 A | 5/1993 | Civerchia |
| 5,374,515 A | 12/1994 | Parenteau et al. |
| 5,522,888 A | 6/1996 | Civerchia |
| 5,716,633 A | 2/1998 | Civerchia |
| 5,827,641 A | 10/1998 | Parenteau et al. |
| 5,919,185 A | 7/1999 | Peyman |
| 6,036,683 A | 3/2000 | Jean et al. |
| 6,187,053 B1 | 2/2001 | Minuth |
| 6,280,435 B1 | 8/2001 | Odrich et al. |
| 6,280,469 B1 | 8/2001 | Terry et al. |
| 6,391,055 B1 | 5/2002 | Ikada |
| 6,551,307 B1 * | 4/2003 | Peyman ......................... 606/5 |
| 2003/0018347 A1 | 1/2003 | Pallikaris et al. |
| 2003/0018348 A1 | 1/2003 | Pallikaris et al. |

FOREIGN PATENT DOCUMENTS

WO  WO 03/009789  2/2003

OTHER PUBLICATIONS

Chen, K–H. et al. (2000). "Transplantation of Adult Human Corneal Endothelium Ex Vivo: A Morphologic Study," *Cornea* 20(7):731–737.

Joo, C–K et al. (2000). "Repopulation of Denuded Murine Descemet's Membrane with Life–Extended Murine Corneal Endothelial Cells as a Model for Corneal Cell Transplantation," *Graefes Archive for Clinical and Experimental Ophathalmology* 238(2):174–180.

Schwab, I. R. and Isseroff, R. R., (2000). "Bioengineered Corneas—The Promise and the Challenge," *New England Journal of Medicine* 343(2):136–138.

Tsai, R. J.–F. et al. (2000). "Reconstruction of Damaged Corneas by Transplantation of Autologous Limbal Epithelial Cells" *New England Journal of Medicine* 343(2):86–93.

* cited by examiner

Primary Examiner—Thomas Barrett
(74) Attorney, Agent, or Firm—Morrison & Foerster LLP

(57) ABSTRACT

This relates to a lens made of donor corneal tissue suitable for use as a contact lens or an implanted lens, to a method of preparing that lens, and to a technique of placing the lens on the eye. The lens is made of donor corneal tissue that is acellularized by removing native epithelium and keratocytes. These cells optionally are replaced with human epithelium and keratocytes to form a lens that has a structural anatomy similar to human cornea. The ocular lens may be used to correct conditions such as astigmatism, myopia, aphakia, and presbyopia.

20 Claims, 6 Drawing Sheets

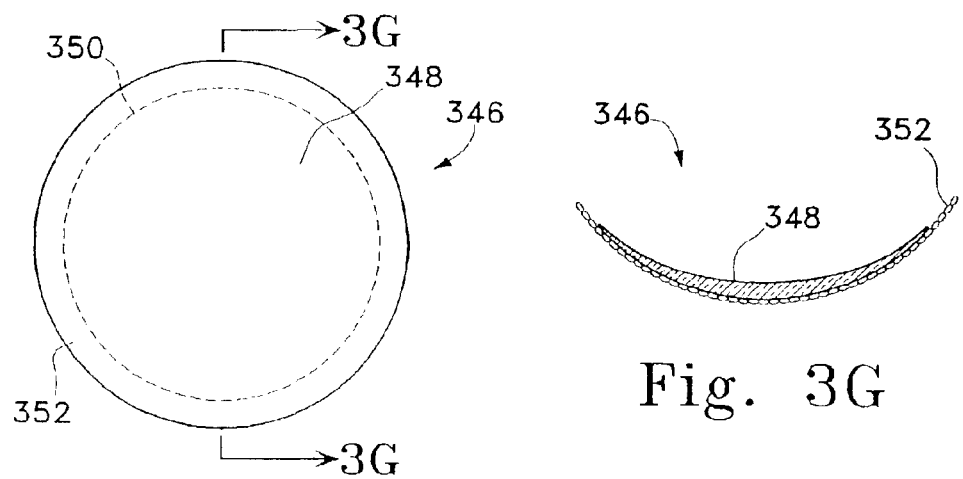
Fig. 3F
Fig. 3G
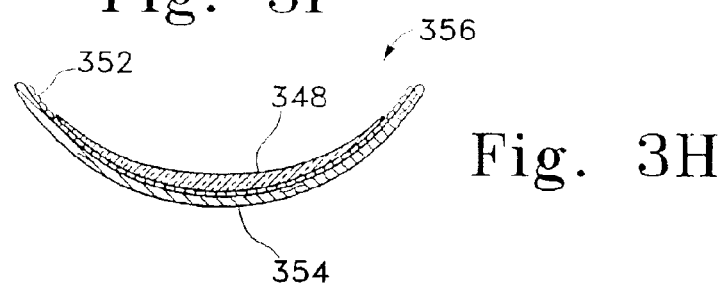
Fig. 3H
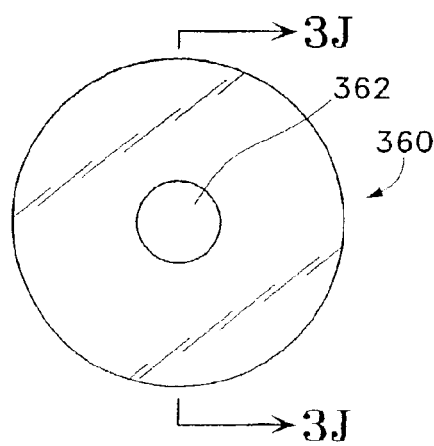
Fig. 3I
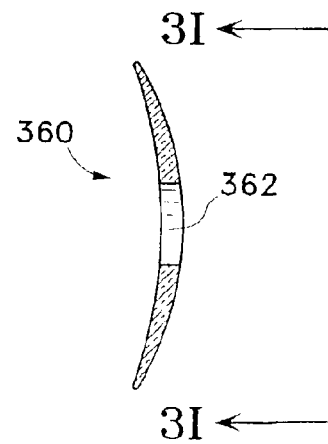
Fig. 3J

METHOD OF LIFTING AN EPITHELIAL LAYER AND PLACING A CORRECTIVE LENS BENEATH IT

RELATED APPLICATIONS

This is a continuation of PCT Application No. PCT/US01/22633, having an International Filing Date of Jul. 18, 2001 and a continuation-in-part of U.S. patent application Ser. No. 09/618,580, filed Jul. 18, 2000 now U.S. Pat No. 6,544,286.

FIELD OF THE INVENTION

This invention is in the field of ophthalmology. More particularly, it relates to a living lens, suitable for use as a contact lens or for subepithelial implantation. The lens is made of donor corneal tissue. The invention includes methods of preparing that lens and to techniques of placing the lens on the eye.

BACKGROUND OF THE INVENTION

The visual system allows the eye to focus light rays into meaningful images. The most common problem an ophthalmologist or optometrist will encounter is that of spherical ammetropia, or the formation of an image by the eye which is out of focus with accommodation due to an improperly shaped globe. The ophthalmologist or optometrist determines the refractive status of the eye and corrects the optical error with contact lenses or glasses.

Many procedures have been developed to correct spherical ammetropia by modifying the shape of the cornea. Light entering the eye is first focused by the cornea, which possesses approximately 75% of the eye's overall refractory power. The majority of refractive operations involve either decreasing or increasing the anterior curvature of the cornea.

The procedures in early corneal refractive surgery such as keratophakia and keratomileusis were originally developed to correct myopia and involved removing a corneal disc from the patient with a microkeratome. The removed corneal disc was then frozen prior to reshaping the posterior surface with a cryolathe. After thawing, the disc was returned to the eye and secured with sutures.

Epikeratophakia, as described in U.S. Pat. No. 4,662,881, is a procedure that involves inserting a precut donor corneal tissue lens with beveled edges into corresponding grooves in recipient cornea. The lens is then sutured to the corneal bed. The donor lens is lyophilized and requires rehydration before placement on recipient cornea.

These techniques and their variations were generally considered to be unsuccessful due to frequent complications involving irregular astigmatism, delayed surgical healing, corneal scarring, and instability of the refractive result. The problems were attributed to the technical complexity of the procedures as well as to the distortion in architecture of the corneal tissue secondary to lens manipulation. For example, in epikeratophakia, epithelial irregularity is induced by lyophilization of the donor lens. Freezing of the lenticule in keratophakia and keratomileusis also causes severe damage to epithelial and stromal cells and disrupts the lamellar architecture of the cornea.

The present invention is a pre-fabricated lens made of donor corneal tissue obtained from tissue sources such as human or animal cornea. The lens is a corneal disc that is preferably shaped on the posterior surface generally to conform in shape to the eye's anterior surface. The inventive lens may be shaped by an ablative laser, e.g., by an excimer laser or other suitable laser. The corneal lenticule is living tissue that has not been frozen, lyophilized, or chemically modified, e.g., fixed with glutaraldehyde to crosslink corneal tissue. Pre-existing keratocytes are removed and then replaced with human keratocytes to decrease antigenicity. After removal of epithelium in the central zone of the recipient's cornea, the lens is placed on this zone in the same manner that a contact lens is placed on the eye.

Ocular lenses found in the prior art do not use native cornea, but are formulated using soluble collagen such as collagen hydrogels, e.g., polyhydroxyethylmethacrylate, or other biocompatible materials. For example, in U.S. Pat. No. 5,213,720, to Civerchia, soluble collagen is gelled and crosslinked to produce an artificial lens. In addition to hydrogels, U.S. Pat. No. 4,715,858, to Lindstrom, discloses lenses made from various polymers, silicone, and cellulose acetate butyrate.

In the cases where ocular lenses use corneal tissue, the lenses are either corneal implants or require a separate agent to adhere the lens to the corneal bed. U.S. Pat. No. 5,171,318, to Gibson et al., and U.S. Pat. No. 5,919,185, to Peyman, relate to a disc of corneal tissue that is partially or entirely embedded in stroma. The ocular lens device disclosed in U.S. Pat. No. 4,646,720, to Peyman et al., and U.S. Pat. No. 5,192,316, to Ting, is attached to recipient cornea with sutures. The corneal inlay described in U.S. Pat. No. 4,676,790, to Kern, is bonded to recipient cornea using sutures, laser welding, or application of a liquid adhesive or crosslinking solution.

The ocular lens device of this invention does not alter the anatomical structure of corneal tissue. U.S. Pat. No. 4,346,482, to Tennant et al., discloses a "living contact lens" consisting of donor cornea that has been anteriorly curved for correction of vision. However, this lens is frozen prior to reshaping on a lathe which results in stromal keratocyte death. U.S. Pat. No. 4,793,344, to Cumming et al., also describes a donor corneal tissue lens that is modified by treatment with a glutaraldehyde fixative that preserves the tissue and prevents lens swelling. This treatment alters the basic structure of the corneal lenticule by crosslinking the tissue.

Furthermore, the cited documents do not show any methods of lens preparation that remove native corneal tissue cells and replace them with cells cultivated from human cornea. My inventive device is devitalized of native epithelium and keratocytes to create an acellular corneal tissue, and then revitalized with human epithelium and keratocytes. An attempt to construct a so-called "corneal tissue equivalent" was shown in U.S. Pat. No. 5,374,515, to Parenteau et al. However, the collagen used in that "equivalent" is obtained from bovine tendon instead of from cornea. The added keratocytes and epithelium are also not from human sources. The tissue using these cell culturing procedures is also quite fragile.

An excimer laser is used to reform a cornea via the "laser in situ keratomileusis" (LASIK) procedure. In this technique, an excimer laser is used to perform stromal photoablation of a corneal flap or in situ photoablation of the exposed stromal bed. Studies have shown that the inaccuracy of correction by this procedure may be as much as one diopter from the desired value. Lenses (contacts and spectacles), in contrast, are able to correct within 0.25 diopters of the desired value.

U.S. Pat. No. 6,036,683, to Jean et al., shows the use of a laser to reshape the cornea. However, the laser changes the native structure of the cornea by irreversibly coagulating collagen. Post-laser relaxation of collagen is not possible with this treatment.

This invention, however, in some variations relates to a pre-fabricated donor contact lens that adheres to recipient cornea without sutures. The lens preserves the anatomy of normal corneal tissue. The donor lens may be obtained from human and animal sources, is devitalized of native keratocytes and epithelium to create an acellular tissue, and then optionally revitalized with at least one of human keratocytes and epithelial cells to maintain lens viability and decrease antigenicity. The inventive corneal overlay technique may be completed under local anesthesia as well as general anesthesia, and the availability of a precut lens will greatly decrease procedure time, patient cost, and risk of operative complications. The duration of healing will also be reduced due to the implementation of a lens already repopulated with keratocytes.

None of the cited documents shows or suggest my invention as described herein.

SUMMARY OF THE INVENTION

This invention is a pre-fabricated ocular lens device having a lens core made of donor corneal tissue from tissue sources such as human or animal cornea. The device may be used as a contact lens or as an implanted lens and may have a generally convex anterior surface and, optionally, a concave posterior surface. The stroma portion of the lens core may be repopulated with replaced keratocytes and the anterior surface is preferably covered with a replaced epithelium. The lens core adheres to recipient cornea without sutures or other adhering materials.

The lens core may be variously used to correct astigmatism, myopia, aphakia, and presbyopia. The lens core may be made of transgenic or xenogenic corneal tissue. Properly treated, the inventive lens may have a clarity at least 85% of that of human corneal tissue of a corresponding thickness. The lens core is not frozen, lyophilized, or chemically treated with a fixative. However, variations of the device may contain therapeutic agents, growth factors, or immunosuppressive agents.

Another component of the invention is a method for preparing the lens device. After sharp dissection of a lenticule from donor corneal tissue, the posterior surface is shaped using an ablative laser, such as an excimer laser or other suitable shaping lasers. Native epithelium and keratocytes are removed and then replaced, as desired, with human epithelium and keratocytes.

Another portion of the invention is a method of corneal overlay that involves deepithelialization of a portion of the anterior surface of the recipient cornea and placement of the inventive ocular lens device upon that anterior surface. Another method involves the temporary separation of the epithelial tissue by suction or other procedures and placement of the inventive lens beneath that epithelial tissue.

BRIEF DESCRIPTION OF THE DRAWINGS

FIG. 3F is a front view of an inventive lens having an overlapping epithelial layer.

FIG. 3G shows a side cross sectional view of the FIG. 3F lens.

FIG. 3H shows a side cross sectional view of an inventive lens in a carrier.

FIG. 3I is a front view of an annular inventive lens.

FIG. 3J shows a side cross sectional view of the FIG. 3I lens.

DETAILED DESCRIPTION

Figure 1:
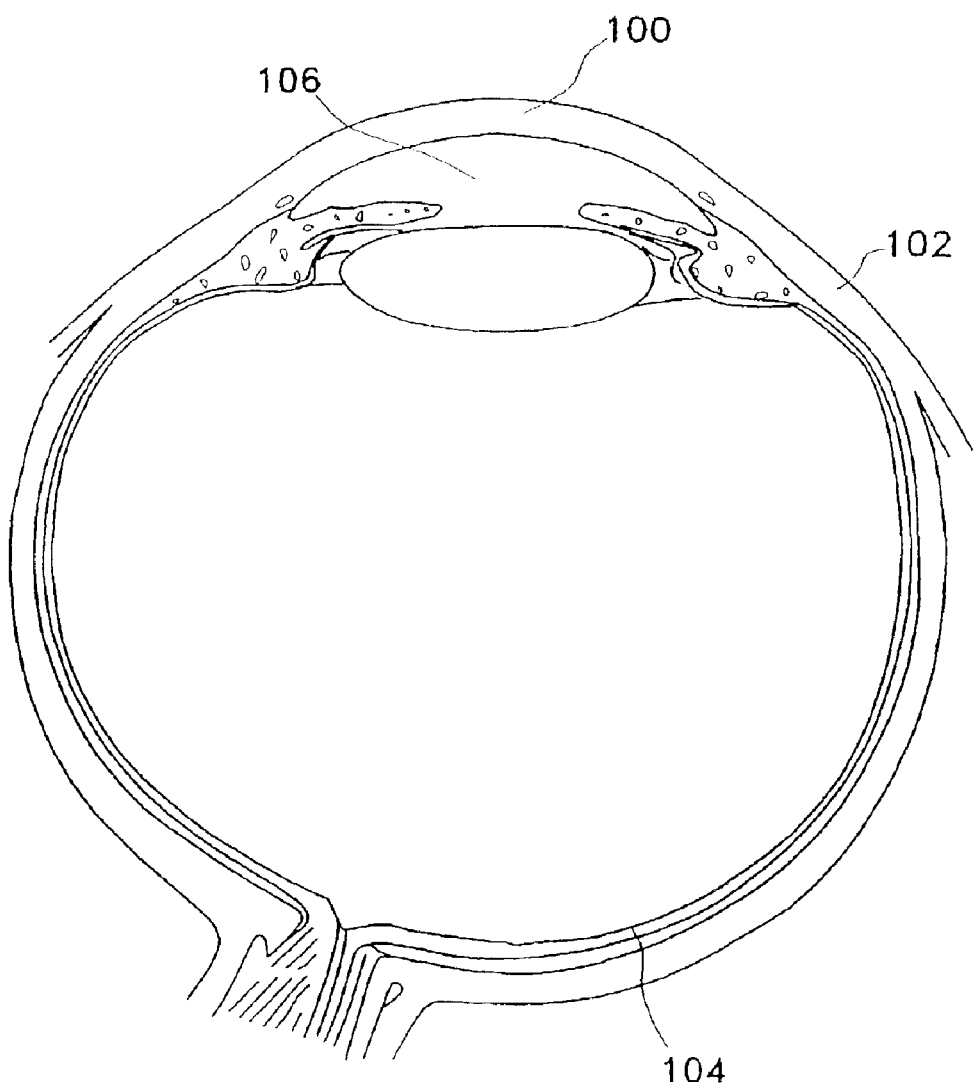
FIG. 1 is a superior, cross-sectional view of the eye.

The eye is designed to focus light onto specialized receptors in the retina that turn quanta of light energy into nerve action potentials. As shown in FIG. 1, light rays are first transmitted through the cornea (100) of the eye. The cornea is transparent due to the highly organized structure of its collagen fibrils. The margins of the cornea merge with a tough fibrocollagenous sclera (102) and is referred to as the corneo-scleral layer.

The cornea (100) is the portion of the corneo-scleral layer enclosing the anterior one-sixth of the eye. The smooth curvature of the cornea is the major focusing power of images on the retina (104) and it provides much of the eye's 60 diopters of converging power. The cornea is an avascular structure and is sustained by diffusion of nutrients and oxygen from the aqueous humor (106). Some oxygen is also derived from the external environment. The avascular nature of the cornea decreases the immunogenicity of the tissue, increasing the success rate of corneal transplants.

The cornea consists of five layers. The outer surface is lined by stratified squamous epithelium which is about five cells thick. Failure of epithelialization results in necrosis of the stromal cap and potential scarring of recipient cornea. The epithelium is supported by a specialized basement membrane known as Bowman's membrane, which gives the cornea a smooth optical surface. The bulk of the cornea, the substantia propria (stroma), consists of a highly regular form of dense collagenous connective tissue forming thin lamellae. Between the lamellae are spindle-shaped keratocytes which can be stimulated to synthesize components of the connective tissue. The inner surface of the cornea is lined by a layer of flattened endothelial cells which are supported by Descemet's membrane, a very thick elastic basement membrane.

Figure 2A:
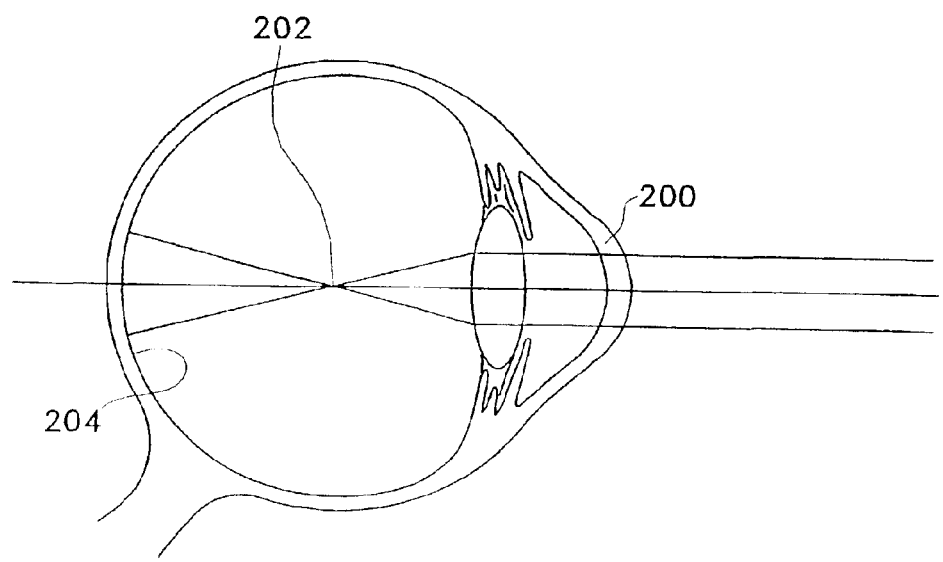
FIG. 2A is a side view of the focusing point in myopia.
Figure 2B:
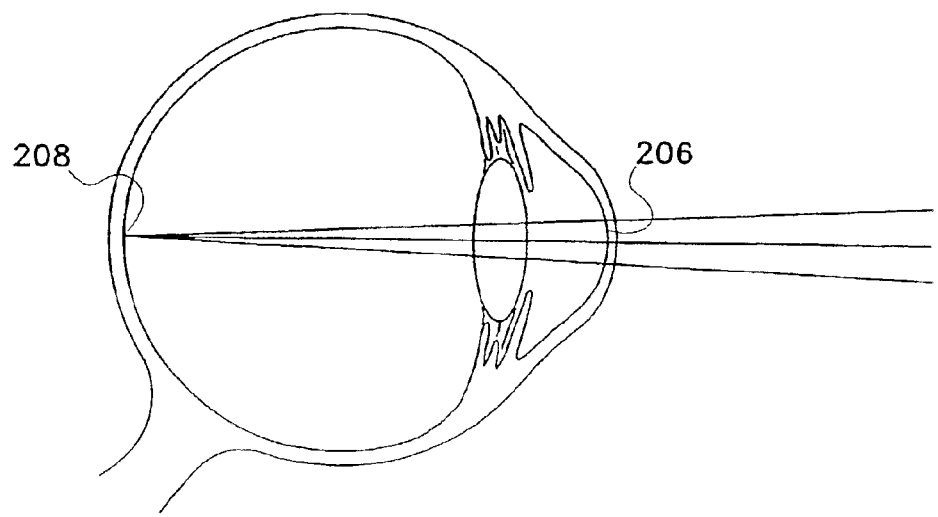
FIG. 2B is a side view of a focusing point corrected by flattening the anterior curvature of the cornea.

As previously mentioned, the focusing power of the cornea is primarily dependent on the radius of curvature of its external surface. In myopia, as seen in FIG. 2A, increased curvature of the cornea (200) causes the focusing point of light rays (202) to fall short of the retina (204). In FIG. 2B, flattening the anterior curvature of the cornea (206) corrects the focal point (208).

Inventive Lens Structures

In a first variation of the inventive lens, the physical shape generally is of a size and configuration that upon installation on the cornea, supplements the curvature of the cornea to correct abnormal conditions such as astigmatism, myopia, hyperopia, presbyopia, and aphakia. Other variations of the lens may be shaped to be placed beneath the anterior surface of the host cornea or to serve as a source of medication.

Typically, the lens core may comprise or consist essentially of acellular donor corneal tissue that has been devitalized, e.g., treated to remove native keratocytes and epithelium, to lessen the chances of tissue rejection and then at least partially revitalized, e.g., treated to introduce at least one of human keratocytes and an epithelial layer, to allow and to support continued use of the inventive lens in place on the eye. It is within the scope of this invention that epithelial cells be (often in the form of a discrete layer) be placed on at least a portion of the anterior surface of the inventive lens. In some variations of the inventive lens, all of the anterior surface will be so-covered. In one variation discussed below, an epithelial layer will extend beyond the periphery of the lens core and optionally the lens be carried in a biodegradable carrier that is used during placement in the eye and later disappears.

The inventive lens may be placed on a host eye from which at least a major portion of the native epithelium on that cornea, has been removed. Preferably in this variation of the inventive procedure, substantially all of the epithelium has been removed from the region upon which the inventive lens will be sited. The lens may also be placed beneath a layer of epithelium lifted from the eye surface during the procedure of introducing the lens onto the anterior surface of the host cornea or in other instances beneath the surface of the host cornea. The inventive lens may be used variously to correct refraction (because of its shape) or it may be used simply to provide a source of infused medication to the eye.

The donor lenticule or lens core may be obtained from other human (allogeneic) or foreign tissue (xenogenic) sources. Appropriate xenogenic sources include rabbit, bovine, porcine, or guinea pig corneal tissue. The ocular lens cores may also come from transgenic corneal tissue or corneal tissue grown in vitro. In many instances, it is desired that the architecture of the corneal layers in the donated tissue, the normal corneal tissue matrix, e.g., the connective tissue or the stroma, be substantially preserved. The "corneal tissue matrix" is made up of thin layers of collagen fibrils. The term "donor corneal tissue", as used here, is meant to include donor or harvested corneas or corneal tissue containing the "corneal tissue matrix". Additionally, in most variations of the invention, it is highly desirable to preserve the anterior surface of the donated corneal tissue as found beneath the native epithelium. The donor corneal tissue is not to undergo harsh treatments such as lyophilization, freezing, or other chemical fixation. Nevertheless, it is sometimes desirable to utilize only a portion of the anterior surface of the donor lens, e.g., in those instances where the inventive lens structure is annular in shape.

The ocular lens device of this invention desirably includes Bowman's membrane, where the donor tissue includes it, to maintain the native structure of human epithelium. Again, it is highly desirable to harvest from donor sources in such a way that the native anterior surface below the epithelium is preserved. I have found that these native structures have a superior ability, particularly after the revitalization steps discussed below, to support and to maintain the replaced epithelium also discussed below. The clarity of the inventive tissue lens core handled in such a way generally will be at least 85%, preferably between 75%–100%, and most preferably at least 90%, of that of human corneal tissue of corresponding thickness.

The overall diameter of the inventive lens is functionally appropriate to perform the desired correction, and generally is less than about 25 mm and more preferably is between 10 and 15 mm. The thickness of the resulting lens is, again, functionally appropriate to perform the desired correction, e.g., generally less than 300 $\mu$m, more preferably between 5–100 $\mu$m.

Figure 3A:
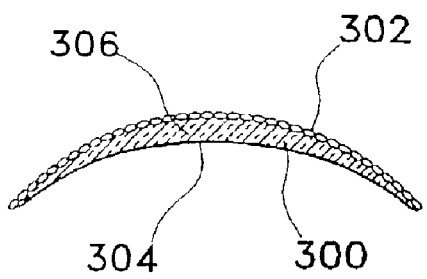
FIG. 3A is a side, cross-sectional view of a pre-fabricated donor lens.
Figure 3B:
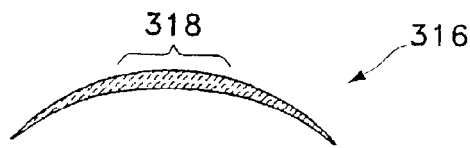
FIG. 3B is a side, cross-sectional view of a pre-fabricated donor lens suitable for correcting myopia.
Figure 3C:
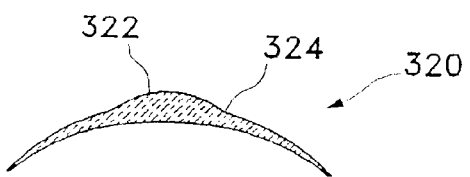
FIG. 3C is a side, cross-sectional view of a pre-fabricated donor lens suitable for correcting aphakia.

As shown in FIG. 3B, a lens core (316) for myopic patients is formed, preferably using the procedures discussed below, in such a way that a generally circular region (318) in the center is flattened in its anterior curvature. In correction of aphakia, a lens such as is shown in FIG. 3C is formed having a comparatively thicker center (322) and a thinner perimeter (324). In general, the shapes discussed here are similar to those found in the so-called "soft" contact lenses and instruction may be had from that technology relating to the overall form of the lenses selected for correcting specific ocular maladies.

Figure 3D:
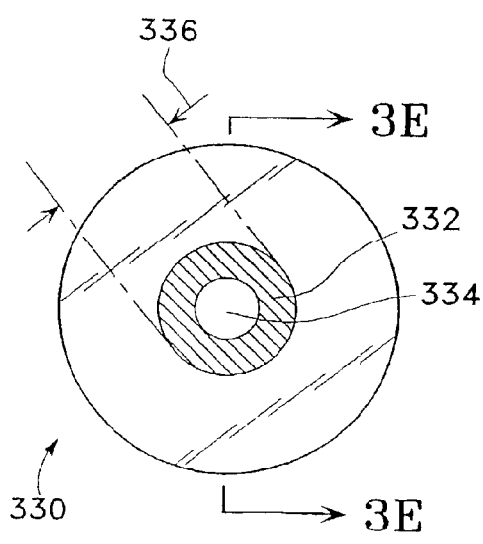
FIG. 3D is a front view of a pre-fabricated donor lens suitable for bifocal use.
Figure 3E:
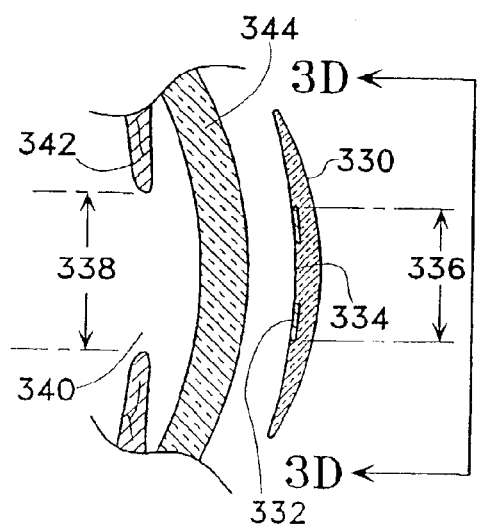
FIG. 3E is a side, cross-sectional view of the FIG. 3C lens positioned away from the cornea of an eye.

As shown in FIGS. 3D and 3E, the inventive lens may also be used to correct presbyopia. In particular, to treat presbyopia, the lens (330) is also provided with an generally opaque annular region (332) adjacent the center of the device. The open center (334) preferably has plano-lens characteristics and an effective diameter of less than about 1.5 mm, preferably between about 0.5–1.5 mm, and most preferably between 0.75 mm and 1.75 mm. The diameter of that open center (334) or central area or "pinhole" is generally formed and selected to be less than the pupillary diameter of the host eye in daylight. This creates a "pinhole" effect, thereby lengthening the overall effective focal length of the eye and minimizing the need for the eye to accommodate. Other bifocal lens designs can also be incorporated, e.g., concentric rings, segmented or sectors of the annular region or ring, or progressive diffractive.

FIG. 3E shows a side, cross-sectional view of the inventive lens (330) shown in FIG. 3D, adjacent the anterior surface of a cornea (344) to illustrate certain features of this variation. The outer diameter (336) of the opaque annular ring (332) is generally selected so that it is smaller than the diameter (338) of the pupil (340) in the iris (342) in low light conditions. In this way, the eye's cornea and lens and the inventive lens cooperate in such a way that incident light passes both though the center of the opaque ring (334), but more importantly, around the periphery of the opaque ring (332), to allow corrected sight during low light conditions.

The annular ring (332) may be situated on the lens core either by placement of a suitable dye, i.e., by "tattooing", or by placement of a substantially opaque biocompatible member of, e.g., Dacron mesh or the like, on the posterior surface to filter light rays. Other placements of the annular ring (332) may be envisioned, e.g., on the anterior surface of the inventive lens. The annular ring (332) itself preferably is quite opaque, e.g., passing less than about 80% of incident visible light, but may be chosen in such a way to be less opaque or to correct other maladies such as colorblindness by shifting an incident color into a visible range by color refraction or the like.

As is shown in FIGS. 3F (in front view) and 3G (in cross section), another variation of the inventive lens device (346) includes a core lens (348) as discussed above but having an epithelial layer (352) that extends beyond the periphery (350) of that lens core (348). The method for producing the variation (346) with an extra-periphery epithelial layer (352) is similar to the method described elsewhere herein except that the lens core (348) is desirably placed in a carrier (354 in FIG. 3H)) having a shape generally conforming to the anterior surface of the donor core lens (348).

The carrier (354), as shown in FIG. 3H, desirably serves several functions. First, it provides a substrate for growth of the epithelial layer (352) prior to the time that the core lens (348) is placed on that epithelial layer (352). This extra surface beyond the periphery of the core lens (348) provides support for the otherwise fragile epithelial layer (352). The carrier (354) may be placed in or formed in a properly shaped receptacle that, in turn, provides support for the fragile carrier (354) during the steps of growing an epithelial layer (352).

The combination (356) of carrier (354), epithelial layer (352)—whether the epithelial layer (352) extends beyond the periphery of the core lens (348) or not, e.g., the epithelial layer (352) is situated only on some or all of the core lens (348)—and core lens (348) placed on that epithelial layer (352), as shown in FIG. 3H, is another variation of the invention. The construct (356) shown in FIG. 3H may, upon proper choice of materials for the carrier, be placed directly in the host eye thereby providing support for the epithelial layer (352) and core lens (348), as well as optionally, medication or other treatment materials for the eye during initial placement.

When the carrier is used for placement in the eye, the carrier (354) preferably comprises a material meeting two related criteria. First, the material desirably is one that dissolves, erodes, or otherwise shortly clears from the eye to be treated after the combination (356) of the carrier (354), epithelial layer (352), and the donor lens (348) are introduced to that eye. Preferably also, the carrier is of a material that serves as a substrate for a pre-grown epithelial layer. Most desirably, the carrier (354) satisfies both criteria. The carrier (354) may comprise a material such as collagen, gelatin, starch, glucosamine glucans, proteins, carbohydrates, polyanhydrides such as polylactides and polyglycolides, their mixtures and copolymers, polydiaxanone, etc.

The carrier (354) may also be infused with medication or other treatment material, antiangiogenesis materials or the like.

FIGS. 3I and 3J show, respectively, a front view and a side cross sectional view of an inventive lens (360) having a central opening (362) passing through the lens body. Although this lens variation (360) is shown without an epithelial layer, it is within the scope of the invention to so include the layer.

Process for Shaping the Lens

Returning to FIG. 3A, the donor core lens (300) desirably is obtained after slicing corneal tissue from the donor with a microkeratome to form that lens core (300). The donor lens (300) has a structural surface, the anterior surface of the lens core, which serves as the structural surface of the donor corneal tissue. The lens core anterior surface is harvested preferably to retain the Bowman's membrane (where the donor lens contains one) and epithelium (302). The posterior surface (304) of the resulting inventive lens is generally concave in shape, although it need not be so. The anterior surface of the lens may be shaped via a shaping step which preferably involves the use of an ablative laser, such as an excimer laser, to obtain the necessary power of the lens. Another suitable forming step is high pressure water jet cutting.

Sterilization, Devitalization, and Revitalization Steps

Although the order of the process steps outlined below is typical, it should be understood that such steps may be varied as needed to produce the desired result.

Generally, the lens will first be shaped to an appropriate shape as discussed above. The lens core may then be subjected to processes of sterilization, devitalization, and revitalization. Removal of epithelium (de-epithelialization) and keratocytes (acellularization) from the donor lens will be referred to as "devitalization". The addition of human epithelium and keratocytes will be referred to as "revitalization". One desirable method for accomplishing those steps is found just below. Other equivalent methods are known.

Phosphate buffered saline (PBS) with antibiotics, epithelial cell media, and keratocyte media are solutions used during these processes. The "PBS with antibiotics" solution may contain:

PBS with antibiotics
1. Amphotericin B (ICN Biomedicals) 0.625 µg/ml
2. Penicillin (Gibco BRL) 100 IU/ml
3. Streptomycin (Gibco BRL) 100 µg/ml
4. Phosphate buffered saline (Gibco BRL)

The composition of the epithelial cell media may include:

Epithelial cell media
1. Dulbecco's Modified Eagle Media/Ham's F12 media (Gibco BRL) 3:1
2. 10% fetal calf serum (Gibco BRL)
3. Epidermal growth factor (ICN Biomedicals) 10 ng/ml
4. Hydrocortisone (Sigma-Aldrich) 0.4 µg/ml
5. Cholera toxin (ICN Biomedicals) $10^{-10}$ M
6. Adenine (Sigma-Aldrich) $1.8 \times 10^{-4}$ M
7. Insulin (ICN Biomedicals) 5 µg/ml
8. Transferrin (ICN Biomedicals) 5 µg/ml
9. Glutamine (Sigma-Aldrich) $2 \times 10^{-3}$ M
10. Triiodothyronine (ICN Biomedicals) $2 \times 10^{-7}$ M
11. Amphotericin B (ICN Biomedicals) 0.625 µg/ml
12. Penicillin (Gibco BRL) 100 IU/ml
13. Streptomycin (Gibco BRL) 100 µg/ml The composition of the keratocyte media may include:

Keratocyte media
1. DMEM
2. 10% neonatal calf serum (Gibco BRL)
3. Glutamine (Sigma-Aldrich) $2 \times 10^{-3}$ M
4. Amphotericin B (ICN Biomedicals) 0.625 µg/ml Sterilization Step After harvesting the lens core from donor corneal tissue and following the shaping step, the lens may be sterilized, for instance, by immersion into 98% glycerol at room temperature. Three weeks of glycerol treatment inactivates intracellular viruses and any bacteria or fungi. Ethylene oxide gas sterilization may also be used, but tends to induce variable damage to stromal tissue.

Devitalization Step

De-epithelialization

I prefer to de-epithelialize the donor lens by placing it in a one molar solution of salt (preferably sodium chloride) at a temperature from 4 to 25° C. After four to eight hours of incubation, the entire epithelial layer generally will split from the corneal stroma and may be easily removed. Thereafter the lens may be washed in a PBS solution with antibiotics to remove salt and cellular material.

Another method of removing the epithelium is via the use of vacuum. The epithelium may be split from the stroma by means of suction (-100 mm Hg to -450 mm Hg). After fifteen minute to 1 hour, the epithelium typically will separate from the stroma at the basement membrane layer. Thereafter the lens may be washed in a PBS solution with antibiotics to remove salt and cellular material.

Finally, the donor lens may be de-epithelialized by placing it in sterile PBS with antibiotics for four hours and changing the solution many times. The lens core may then be kept submerged in the PBS solution at 37° C. for one week to produce a split between the epithelium and the stroma. The epithelium may then be removed, e.g., by physically scraping or washing with a liquid stream. Small numbers of lenses may be stripped of epithelium by gentle scraping with forceps.

Acellularization

The de-epithelialized lens may be then immersed in a solution of detergent (for example 0.025% to 15% sodium dodecyl sulfate) to wash out the keratocyte cellular material. A detergent will solubilize and wash out the keratinocytic material. This can take place from 1 to 8 hours. Afterward the cellular material can be washed in a buffered solution with antibiotics to remove detergent and cellular material.

Alternatively, the de-epithelialized lens may be immersed in sterile PBS with antibiotics for an appropriate period, e.g., several weeks, perhaps six weeks to remove native keratocytes. The solution may be changed twice weekly. In some instances, it may not be necessary to remove keratocytes from the donor lens, e.g., when the donor tissue is obtained from a transgenic source and has minimal antigenicity.

Revitalization Step

Preparation of Cells

Human epithelial cells and keratocytes are used in the revitalization process. Epithelial cells may be obtained from a tissue bank, but are preferably obtained from fetal or neonatal tissue. Fetal cells are most preferable, since the properties of fetal tissue minimize scarring during any wound healing process.

In any event, freshly isolated epithelial cells, obtained by trypsinization of corneal tissue, may be seeded onto a precoated feeder layer of lethally irradiated 3T3 fibroblasts (i.3T3) in epithelial cell media. Cells are cultured and media changed every three days until the cells are 80% confluent, about 7–9 days. Residual i.3T3 are removed with 0.02% EDTA (Sigma-Aldrich) before the epithelial cells are detached using trypsin (ICN Biomedicals). Another method of regenerating epithelium involves culturing autologous epithelial cells on human amniotic membrane as described in Tsai et al. (2000). "Reconstruction of Damaged Corneas by Transplantation of Autologous Limbal Epithelial Cells," *New England Journal of Medicine* 343:86–93.

Keratocytes may be extracted from the remaining stromal tissue. The stroma is washed in PBS, finely minced, and placed in 0.5% collagenase A (ICN Biomedicals) at 37° C. for 16 hours. Keratocytes obtained from this enzyme digest are then serially cultured in keratocyte media. The epithelial cells and keratocytes generated in the revitalization step will be referred to as "replaced" epithelial cells and keratocytes.

Production of the Donor Lens

The acellular donor lens core may then be placed on a hydrophilic, polyelectrolyte gel for completion of the re-vitalization. The preferred polyelectrolytes are chondroitin sulfate, hyaluronic acid, and polyacrylamide. Most preferred is polyacrylic acid. The lens is immersed in keratocyte media and incubated with approximately $3 \times 10^5$ keratocytes for 48 hours at 37° C. Approximately the same amount of epithelial cells are then added to the anterior stromal surface. Tissue culture incubation continues for another 48 hours. Keratocyte media is changed every two to three days. Once the epithelium is regenerated, the polyelectrolyte gel draws water out of the lens at a pressure of about 20–30 mm Hg until the original lens dimensions are obtained.

Replaced epithelium covers at least a portion of the anterior surface of this variation of the inventive lens and replaced keratocytes repopulate the stroma of the lens core after revitalization.

As noted above, another variation of the inventive lens includes an epithelial layer (352 in FIG. 3G) that extends from the periphery of the lens core (348). The same procedure as just outlined may be used to prepare the epithelial cell layer in the carrier (354) prior to placement of the lens core (348) onto the pre-prepared epithelial cell layer.

It may be beneficial in some instances also to incorporate therapeutic agents, growth factors, or immunosuppressive agents into the lens core further to decrease the risk of rejection or remedy disease states.

Placement of the Lens on the Eye

Figure 4A:
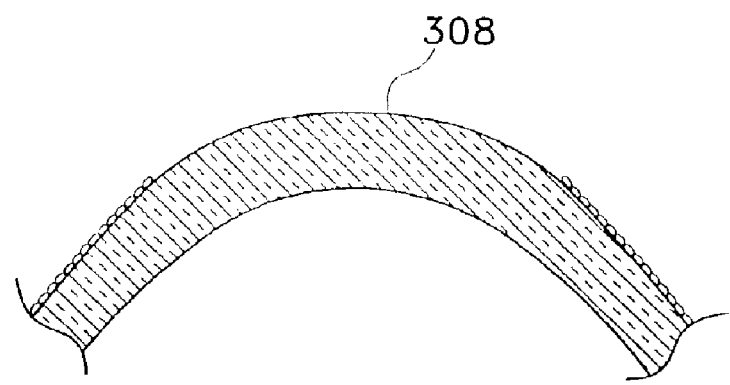
FIG. 4A is a side, cross-sectional view of an area of de-epithelialized recipient cornea prepared to receive the optical lens of the present invention.
Figure 4B:
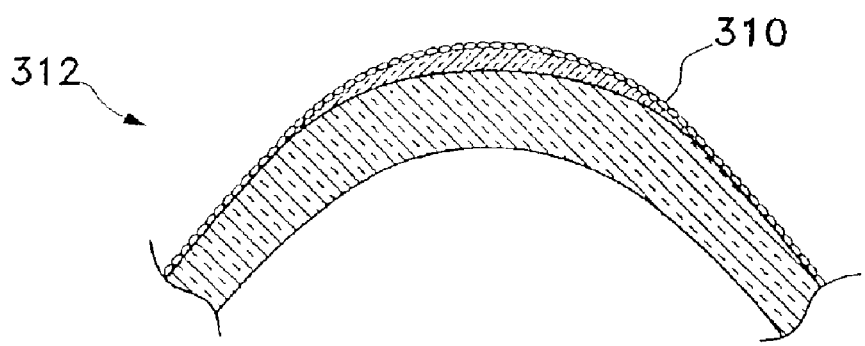
FIG. 4B is a side, cross-sectional view of the donor lens after placement on recipient cornea.

One procedure for applying the lens of this invention is depicted in FIGS. 4A and 4B. During the procedure, the donor lens (300), as shown in FIG. 3A, is placed on a portion of recipient cornea that has been de-epithelialized (308). The result is the placement and construct (312) shown in FIG. 4B. The lens' replaced epithelium and the host epithelium eventually grow to form a continuous, water-tight layer (310). I have found that the inventive lens bonds or adheres to the recipient cornea without sutures or adhesives, but can also be removed without substantial difficulty.

Figure 5:
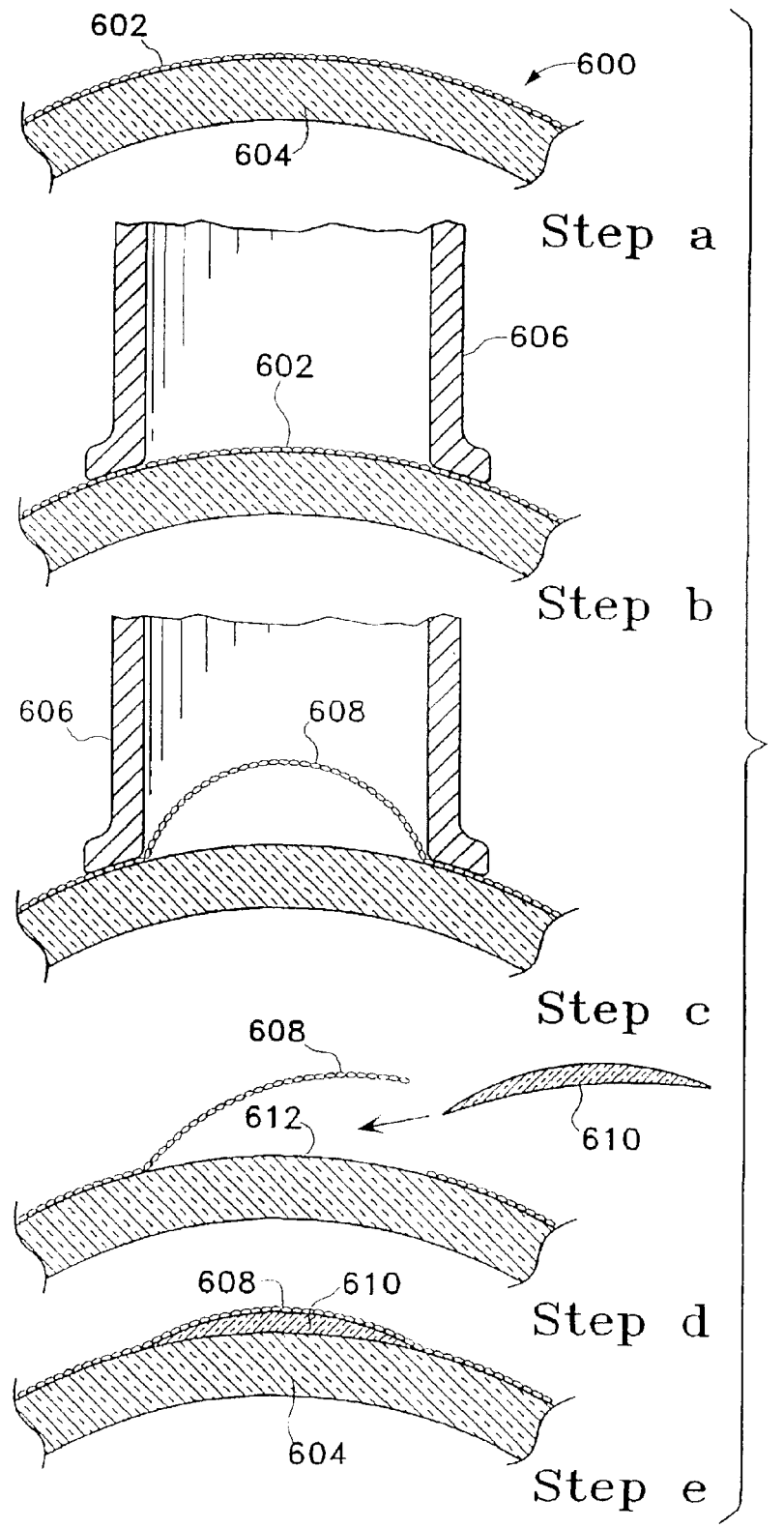
FIG. 5 show a series of steps for introducing an inventive lens subepithelially.

Another placement procedure variation is shown in FIG. 5. In this variation, it is preferable to use a core lens that has been only partially revitalized in that the keratocytes have been replaced but the epithelial layer has not. Of course, a core lens that has been partially covered with a seed layer of epithelial cells is also acceptable. In any event, step a. of FIG. 5 shows a native eye (600) having an epithelial layer (602) and a corneal stroma (604). Step b. of FIG. 5 shows the placement of a suction device (606) on the anterior surface of the eye (600). The suction device (606) applies a modest vacuum to the epithelial layer (602), e.g., between about -100 mmHg and -450 mmHg, to raise a section of the epithelial layer (602) as shown in step c. This blister (608) typically is filled with a physiologic fluid. Obviously, the suction device (606) has a footprint on the surface of the cornea similar to the size of the lens to be placed on that cornea. Step d. shows the opened epithelial flap (608) and the placement of the lens towards the corneal stromal margin (612) beneath that epithelial flap (608). Step c. of FIG. 5 shows the finished placement of the lens (610) on the cornea beneath the native epithelial membrane. This procedure has a number of benefits including that of being less traumatic to the surface of the eye than simple removal of the epithelium.

It is also within the scope of the invention to use the preparation procedure for the LASEK procedure in this invention for the step of exposing the corneal surface for application of the inventive lens. The lASEK procedure is known and, unlike the LASIK procedure, does not involve temporary removal of an anterior flap of corneal tissue with a surgical tool but rather only utilizes an ethanol wash and a temporary withdrawal of the epithelial layer for a laser treatment. Such a preliminary step, the washing with ethanol to perturb the junction between the corneal stroma and the epithelium is adequate to provide a layer of epithelium for temporary movement and insertion of the inventive lens on the corneal surface.

I have described the structural and physiologic properties and benefits of this donor ocular lens. This manner of describing the invention should not, however, be taken as limiting the scope of the invention in any way.

I claim as my invention:

1. A method for acting on an eye having an anterior corneal surface and an epithelial tissue layer, the method comprising:
   a.) lifting from the anterior corneal surface, a portion of the epithelial tissue layer with the portion connected to the corneal surface resulting in a lifted continuous portion of the epithelial tissue layer separated from a corneal stromal margin a lifted continuous,
   b.) placing a corrective ocular device entirely onto the corneal stromal margin from which the epithelial tissue portion has been separated, and
   c.) placing the lifted epithelial portion onto the corrective ocular device.

2. The method of claim 1 wherein said lifting step comprises employing vacuum to lift the epithelial layer from the anterior surface.

3. The method of claim 1 wherein the step of introducing a corrective ocular device onto the corneal anterior surface comprises introducing a lens core containing donor corneal tissue with a generally convex anterior surface and a posterior surface and where the lens core comprises replaced keratocytes in said lens core.

4. The method of claim 3 wherein the lens core comprises acellular corneal tissue.

5. The method of claim 3 wherein the lens core consists essentially of acellular corneal tissue.

6. The method of claim 3 wherein the lens core comprises human corneal tissue.

7. The method of claim 3 wherein the lens core comprises allogenic corneal tissue.

8. The method of claim 3 wherein the lens core comprises xenogenic corneal tissue.

9. The method of claim 8 wherein the xenogenic lens core comprises corneal tissue selected from the group consisting of rabbit, bovine, porcine, and guinea pig corneal tissue.

10. The method of claim 3 wherein the lens core comprises transgenic corneal tissue.

11. The method of claim 3 wherein the lens core further contains a therapeutic agent, immunosuppressive agent, or growth factors.

12. The method of claim 3 wherein the lens core has not been frozen, lyophilized, or chemically treated by a fixative.

13. A method for acting on an eye having an anterior corneal surface and an epithelial tissue layer, comprising the steps of:
   a.) lifting from that corneal surface with a device, a living portion of the epithelial tissue layer with the portion connected to the corneal surface resulting in a lifted continuous portion of the epithelial tissue layer separated from a corneal stromal margin,
   b.) removing the device and leaving the lifted epithelial portion connected to the corneal surface;
   c.) introducing a corrective ocular device entirely onto the corneal stromal margin from which the epithelial tissue portion has been seperated, and
   d). placing the lifted epithelial portion onto the corrective ocular device.

14. The method of claim 13 wherein the lifting step comprises employing a vacuum to lift the epithelial layer from the anterior surface.

15. The method of claim 13 wherein the step of introducing a corrective ocular device onto the corneal anterior surface comprises introducing a lens core containing donor corneal tissue with a generally convex anterior surface and a posterior surface and where the lens core comprises replaced keratocytes in said lens core.

16. The method of claim 15 wherein the lens core comprises acellular corneal tissue.

17. The method of claim 15 wherein the lens core consists essentially of acellular corneal tissue.

18. The method of claim 15 wherein the lens core comprises a member selected from the group consisting of human corneal tissue; allogenic corneal tissue; xenogenic corneal tissue; transgenic corneal tissue; and corneal tissue selected from the group consisting of rabbit, bovine, porcine, and guinea pig corneal tissue.

19. The method of claim 15 wherein the lens core further contains a therapeutic agent, immunosuppressive agent, or growth factors.

20. The method of claim 15 wherein the lens core has not been frozen, lyophilized, or chemically treated by a fixative.

* * * * *